United States Patent
Detje

(10) Patent No.: US 7,278,850 B2
(45) Date of Patent: Oct. 9, 2007

(54) DENTAL IMPRESSION TRAY

(75) Inventor: Bernd Detje, Hamburg (DE)

(73) Assignee: Ernst Muhlbauer GmbH & Co. KG, Norderfriedrichskoog (DE)

( * ) Notice: Subject to any disclaimer, the term of this patent is extended or adjusted under 35 U.S.C. 154(b) by 318 days.

(21) Appl. No.: 10/433,355

(22) PCT Filed: Jun. 7, 2002

(86) PCT No.: PCT/EP02/06267

§ 371 (c)(1),
(2), (4) Date: Jun. 3, 2003

(87) PCT Pub. No.: WO02/100291

PCT Pub. Date: Dec. 19, 2002

(65) Prior Publication Data

US 2004/0043353 A1 Mar. 4, 2004

(30) Foreign Application Priority Data

Jun. 13, 2001 (DE) .................................. 101 28 719

(51) Int. Cl.
*A61C 11/00* (2006.01)
*A61C 9/00* (2006.01)
(52) U.S. Cl. ........................ 433/213; 433/214
(58) Field of Classification Search .................. 433/37
See application file for complete search history.

(56) References Cited

U.S. PATENT DOCUMENTS

| 2,311,158 A | 2/1943 | Conway et al. |
| 5,718,577 A | 2/1998 | Oxman et al. |
| 6,394,802 B1 * | 5/2002 | Hahn ........................ 433/37 |
| 6,758,671 B2 * | 7/2004 | Brattesani .................. 433/37 |

FOREIGN PATENT DOCUMENTS

| DE | 41 16 190 A1 | 5/1991 |
| DE | 196 08 546 A1 | 3/1996 |
| WO | WO 02/100291 A1 | 12/2002 |

\* cited by examiner

*Primary Examiner*—Cris Rodriguez
*Assistant Examiner*—Candice C. Stokes
(74) *Attorney, Agent, or Firm*—Alix, Yale & Ristas, LLP

(57) ABSTRACT

The invention relates to a dental impression tray comprising a base and at least two walls defining said base. At least one of these walls is at least partially formed by hollow bodies made of flexible material. Said hollow bodies can be filled in order to form, when taut, the desired shape for using the mould tray. In order to provide sufficient longitudinal stability for the impression tray, at least one of the walls is fitted with a rigid longitudinal rib. Said wall can also be rigid in its entirety. The hollow bodies which are to be filled can be fitted with openings. The moulding material filling the hollow bodies can flow from said openings into the moulding region of the dental impression tray. The base is flexible.

17 Claims, 1 Drawing Sheet

DENTAL IMPRESSION TRAY

CROSS REFERENCE TO RELATED APPLICATION

This application is a 371 of PCT/EP02/06267 filed Jun. 7, 2002.

BACKGROUND OF THE INVENTION

To obtain impressions of teeth in order to produce a denture, use is made of impression compounds which harden from a pasty state. In order to hold the impression compound in the area of the teeth from which the impression is being taken, impression trays are used. These consist of a base and of at least two side walls which together enclose the impression area into which the impression compound is introduced so as to be brought, held by the tray, to the impression site. The walls, one of which comes to lie on the lingual/palatal aspect and the other on the buccal aspect of the teeth from which the impression is to be taken, are intended to ensure that the compound cannot flow out but is instead held at the sides of the teeth from which the impression is to be taken. It is known (DE-A-196 08 546) to provide, in the tray, a delivery tube for the compound, which delivery tube is provided with a row of outlet openings distributed along the length of the tray.

As a result of the closing of the dentition during impression-taking, the teeth from which the impression is to be taken force themselves into the impression compound. This is not successfully accomplished if the patient bites on one of the two walls and, accordingly, the teeth from which the impression is to be taken do not penetrate into the space between the walls. This risk arises in known impression trays which are made of a rigid material such as metal or plastic. If, according to a known proposal (DE-C-31 04 721), the compound is enclosed entirely within a flexible tube, the tube material located between the compound and the teeth forms an obstacle to a clean impression. Furthermore, the unpublished prior art includes the proposal that fixed walls be avoided by means of the walls being formed by inflatable tube elements.

Compressed air, water or else impression compound can be used to fill the tube elements. However, it has been found that, on account of the lack of shape stability of such impression trays, the impression compound is not securely held and, for example, flows out over the walls. The impression material does not then attain the desired height, and the impression-taking is not completely successful.

SUMMARY OF THE INVENTION

Accordingly, provision is made for at least one of the walls to have a rigid longitudinal rib. This longitudinal rib can form part of the wall, which is otherwise formed for example by a tube element which is to be filled, or it can be an insert of such a tube. It can also form the whole of the wall in question. The wall which is of rigid design or is equipped to be rigid is preferably the wall located on the lingual/palatal aspect. However, instead of or in addition to this, the wall on the buccal aspect can also be equipped to be rigid. The base of the tray is formed by flexible material. Apart from avoiding the disadvantages of the prior art, this ensures that the tray can be packed within a very small space and can easily be made ready for use.

The wall which is erected by filling comprises at least one tube element whose interior communicates with a filling opening. This filling opening can for example be attached to a dispensing appliance for impression compound. To use the tray, the tube element is filled with the impression compound and thereby assumes the taut and sufficiently shape-stable state.

As soon as the impression tray has reached this state, its impression area can be provided in a customary manner with the required amount of impression compound, for example by being held under the nozzle of a suitable dispensing appliance. According to the invention, it is more advantageous if the tube element to be filled with the impression compound has at least one outflow opening directed toward the impression area of the tray. After the tube element has been filled, the impression compound passes through this opening and into the impression area of the tray and finally fills the latter. A row of such outflow openings is expediently distributed along the length of the impression area of the tray so as to achieve uniform filling. If the tube element is arranged only on one side of the tray, it is provided with these outflow openings on its side directed toward the impression area. In order to achieve a complete and sufficiently rigidifying filling of the tube element, it may be more expedient, however, to guide this around the narrow end of the tray directed away from the filling opening and even, if appropriate, route it back on the other side. Substantially the whole length of the wall in question should lie between the filling opening and the outflow opening so that it becomes taut as a result of the pressure drop in the outflow opening or outflow openings before the material can flow into the impression area. If the tube element in the area of the rigid wall is routed back in the direction toward that end of the tray provided with the filling opening, the outflow openings are expediently arranged on the side of the rigid wall.

When it flows out of the tube element into the impression area of the tray, the compound should meet a certain resistance, which ensures that, at least during the filling procedure, a certain overpressure prevails in the tube element and guarantees the tautness and rigidity of the tube element. Slit-shaped outlet openings have proven expedient, preferably extending in the transverse direction (relative to the direction of the tube element). According to another feature of the invention, the outflow openings can form mouths or channels or nozzles projecting into the impression area of the tray. On the one hand, this guarantees a particularly uniform filling of the impression area, on the other hand it creates the desired pressure difference. Finally, according to the invention it is possible to provide the outflow opening(s) with a burstable seal, for example a burstable membrane. The burstable seal opens only when a predetermined overpressure is reached in the tube element, so that its tautness is in this way ensured.

It is recommended to ensure complete filling of the tube element with impression compound, and this presupposes removal of air. If outflow openings toward the impression area of the tray are provided, the air is removed through these outflow openings. Tube elements with a blind end should be provided with a special vent hole which is expediently designed in such a way that it prevents impression compound being pressed out. This can be achieved, for example, by the vent hole being very small or being provided with a suitable valve.

The filling opening is expediently designed for fitted attachment to a dispensing appliance for impression compound. If the dispensing nozzle of this appliance ends in a cone shape, a tube end forming the filling opening can for example be pushed onto the conical nozzle end. A form-fit coupling can also be provided, for example with a bayonet catch and sealing surfaces. During handling of the tray, escape of impression compound from the filling opening must be prevented. This can be achieved using a self-closing valve, for example, analogously to the design of the filling valve, so-called valve sacks. A special closure clip can also be provided which is placed from outside onto the tube part forming the filling openings in order to press it together. Or a stopper can be provided. If it is connected to the tube part in a sufficiently shape-stable manner, it can according to the invention be provided with a grip via which the entire tray can be handled.

BRIEF DESCRIPTION OF THE DRAWINGS

The invention is explained in more detail below with reference to the drawing which depicts advantageous illustrative embodiments. In the drawing.

DETAILED DESCRIPTION OF THE PREFERRED EMBODIMENTS

Figure 1:
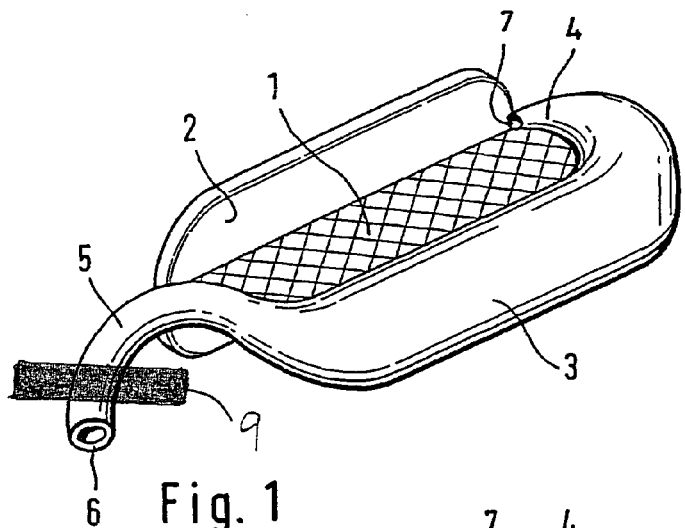
FIG. 1 shows the perspective view of a first embodiment.
Figure 2:
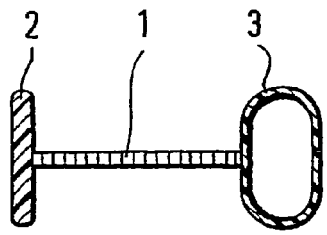
FIG. 2 shows a cross section through the first embodiment.

The impression tray according to FIGS. 1 and 2 has a base 1 which can be formed for example by a flexible foil or a piece of fabric. On the lingual/palatal side, the plate 1 is delimited by a wall 2 formed by a rigid structural part. It is substantially plate-shaped. It forms a longitudinal rib which renders the tray rigid. Rigid in this context is to be understood as meaning a strength which permits a sufficient shape stability of this wall under the forces which occur. Suitable materials are polyethylene, polyvinyl chloride, cardboard or the like.

The base 1 is delimited on the buccal side by a tube element 3. The tube element 3 extends along the entire length of the base 1 and also encloses its rear edge 4. It ends in the connection to the wall part 2. The tube portion 4 ensures the lateral tensioning of the tray between the wall 2 and the tube element 3 when the base 1 is too flexible to be able to satisfy this task.

At the front end, the tube element 3 communicates with a filling tube 5 whose end 6 forms the filling opening. The tube 5 can be pushed with the opening 6 over the conical end of a filler nozzle. Also shown is closing element 9 which can be a self-closing valve, a closure clip, or a stopper with a grip via which the entire tray can be handled.

Provided at the end of the tube element 3 or tube portion 4 there is an opening 7 which points toward the impression area of the tray formed by the base 1. It is either so small that no appreciable amounts of impression compound can escape from it, and it then serves only for removal of air. Or it is so large that the impression compound can flow out in the amount required for the impression and can fill the impression area.

Instead of this, the tube element 3 could also be provided with a plurality of outflow openings along its length which point toward the upper face of the base 1 in order to deliver the required amount of impression compound uniformly to the impression area.

Figure 3:
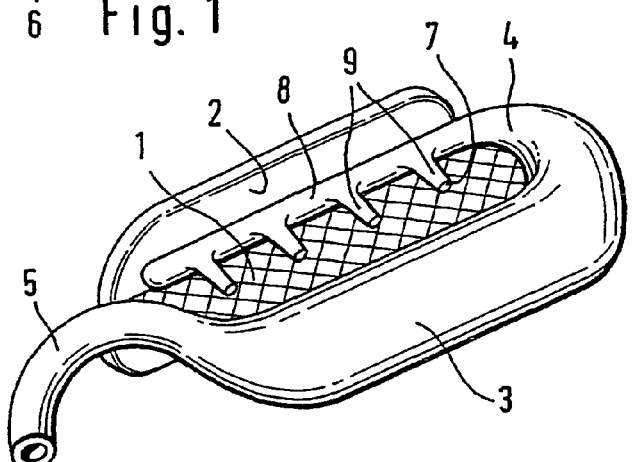
FIG. 3 shows the perspective representation of a second embodiment.
Figure 4:
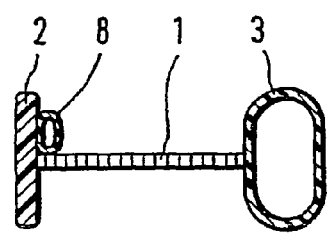
FIG. 4 shows a cross section through the second embodiment.

The illustrative embodiment according to FIGS. 3 and 4 is identical to the above-described embodiment in respect of the base 1, the wall 2, the tube element 3 and the filling tube 5. Adjoining the rear end of the tube element 3 there is once again a tube portion 4 which stiffens the rear narrow end of the device. This is adjoined by a tube element 8 which runs along the inner side of the wall 2 as far as the front end and has a plurality of outflow openings 7 which protrude into the impression area in the form of projecting mouths or nozzles and permit uniform delivery of impression compound to this area.

The filling tube 5, the tube element 3, the tube portion 4 and the tube element 8 can be made in one piece, in which case the different diameters are generated by different expansion.

Figure 5:
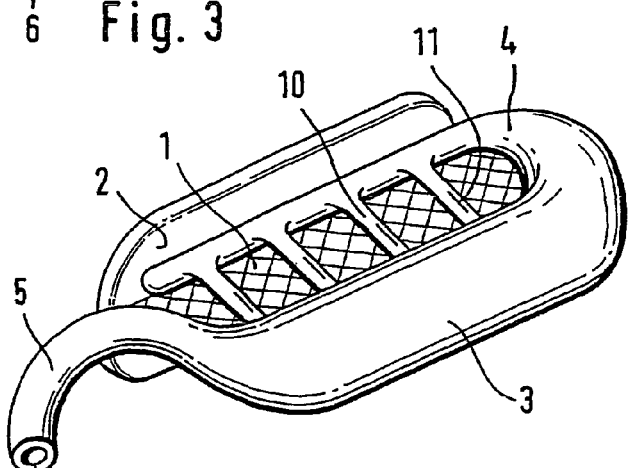
FIG. 5 shows a third embodiment.

In the third embodiment according to FIG. 5, the projecting mouths 9 according to the above-described embodiment are lengthened in the form of channels 10 which extend in uniform distribution transversely across the base 1. They include slit openings 11, of which the drawing indicates one per channel 10. It will be appreciated that several such openings can be distributed across the surface of the base 1. With the slit-shaped configuration of the openings 11, these are expediently arranged transversely with respect to the longitudinal extent of the channels containing them.

The invention claimed is:

1. A dental impression tray having a lingual/palatal side and a generally opposite buccal side, and a base wherein either said lingual/palatal side or said buccal side consists of a first wall and the other said side consists of a second wall, the first wall being stiff in its entirety and forming a longitudinal rib, characterized in that the first wall is substantially plate-shaped, and the second wall is formed of flexible material which is filled with impression compound in order to assume, in a taut state, a stable shape to enable filling of the tray, and the base is being made of flexible material.

2. The tray as claimed in claim 1, characterized in that the first wall is located on the lingual/palatal side.

3. The tray as claimed in claim 2, characterized in that the tillable wall comprises at least one tube element whose interior communicates with a filling opening.

4. The tray as claimed in claim 1, characterized in that it has a tube part with a blind end and with a vent hole.

5. The tray as claimed in claim 4, characterized in that the vent hole is designed as a valve obstructing the outflow of impression compound.

6. The tray as claimed in claim 1, characterized in that the second wall comprises at least one tube element whose interior communicates with a filling opening.

7. The tray as claimed in claim 6, characterized in that the filling opening is designed for fitted attachment to a dispensing appliance for impression compound.

8. The tray as claimed in claim 7, characterized in that the filling opening or the filling tube is provided with a closure device.

9. The tray as claimed in claim 8, characterized in that the closure device is a self-closing valve.

10. The tray as claimed in claim 8, characterized in that the closure device is a closure clip.

11. The tray as claimed in claim 8, characterized in that the closure device is equipped with a grip for the tray.

12. The tray as claimed in claim 6, characterized in that at least one tube element has an interior which communicates with at least one outflow opening directed toward an impression area of the tray.

13. The tray as claimed in claim 12, characterized in that an outflow opening is provided with a burstable seal.

14. The tray as claimed in claim 12, wherein the impression area has a length and characterized in that a row of outflow openings is distributed along the length of the impression area of the tray.

15. The tray as claimed in claim 14, characterized in that a tube element in the area of the rigid wall is routed back in the direction toward that end of the tray provided with the filling opening.

16. The tray as claimed in claim 14, characterized in that the outflow openings are designed as slits.

17. The tray as claimed in claim 14, characterized in that the outflow openings form mouths projecting into the impression area of the tray.

* * * * *

UNITED STATES PATENT AND TRADEMARK OFFICE
CERTIFICATE OF CORRECTION

PATENT NO. : 7,278,850 B2  Page 1 of 1
APPLICATION NO. : 10/433355
DATED : October 9, 2007
INVENTOR(S) : Detje It is certified that error appears in the above-identified patent and that said Letters Patent is hereby corrected as shown below:

<u>Column 4</u>:

Line 39, delete "tillable" and substitute --fillable--.

Signed and Sealed this

Eighteenth Day of March, 2008

JON W. DUDAS
*Director of the United States Patent and Trademark Office*